United States Patent [19]

Nagamine et al.

[11] Patent Number: 5,098,928
[45] Date of Patent: Mar. 24, 1992

[54] KETENDITHIOACETAL DERIVATIVES AND PHARMACEUTICAL COMPOSITIONS CONTAINING THE SAME

[75] Inventors: Masashi Nagamine, Nishinomiya; Kunikazu Hiraga, Osaka; Atsushi Sakai; Matazaemon Uchida, both of Kawachinagano, all of Japan

[73] Assignee: Nihon Nohyaku Co., Ltd., Tokyo, Japan

[21] Appl. No.: 602,932

[22] Filed: Oct. 25, 1990

Related U.S. Application Data

[63] Continuation of Ser. No. 295,365, Jan. 10, 1989, abandoned.

[30] Foreign Application Priority Data

Jan. 14, 1988 [JP] Japan ................................. 63-6303

[51] Int. Cl.⁵ .................. A61K 31/385; C07D 339/08
[52] U.S. Cl. ..................................... 514/436; 514/431; 514/440; 514/255; 544/374; 549/11; 549/21; 549/22; 549/39
[58] Field of Search ................. 549/11, 22, 39, 21; 514/431, 436, 440

[56] References Cited

U.S. PATENT DOCUMENTS 3,525,751  8/1970  Fried ....................................... 549/22
4,348,529  9/1982  Borror et al. ........................... 549/11
4,818,765  4/1989  Weith et al. ............................ 549/35

FOREIGN PATENT DOCUMENTS 0099329   1/1984  European Pat. Off. .
2709504   9/1977  Fed. Rep. of Germany .
52-106815 9/1977  Japan .
53-82749  7/1978  Japan .
59-16887  1/1984  Japan .

OTHER PUBLICATIONS

Chemical Abstracts vol. 90, Abst. No. 22621p, (1979).
Chemical Abstracts vol. 88, Abst. No. 104694n, (1978).
Chemical Abstracts vol. 87, Abst. No. 201,300t, (1977).
Chem. Abst., vol. 93, 1980, p. 716, Abstract No. 7844g.
Tetrahedrom Letters No. 31, pp. 2731-2734, 1976.

*Primary Examiner*—Mary C. Lee
*Assistant Examiner*—Jacqueline Haley
*Attorney, Agent, or Firm*—Cushman, Darby & Cushman

[57] ABSTRACT

The ketenedithioacetal derivatives of formula (I) have a potent hypolipidemic and anti-arteriosclerotic effect and are useful for prophylaxis and treatment of arteriosclerosis or hyperlipidemia.

8 Claims, No Drawings

KETENDITHIOACETAL DERIVATIVES AND PHARMACEUTICAL COMPOSITIONS CONTAINING THE SAME

BACKGROUND OF THE INVENTION

1. Field of the Invention

The present invention relates to ketenedithioacetal derivatives represented by general formula (I):

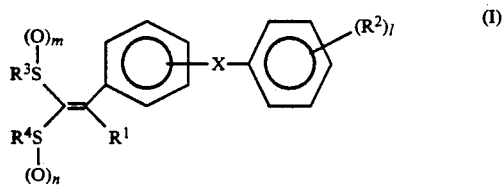

wherein $R^1$ represents a $C_1$- to $C_6$-alkyl group, a $C_2$- to $C_7$-alkoxycarbonyl-$C_1$- to $C_6$-alkyl group, a di($C_1$- to $C_4$-alkyl)amino-$C_1$- to $C_6$-alkyl group or a carboxy-$C_1$- to $C_6$-alkyl group; $R^2$, which may be the same or different, independently represents a hydrogen atom, a halogen atom, a $C_1$- to $C_6$-alkyl group (whose group is optionally substituted with a $C_2$- to $C_7$-alkoxycarbonyl group, a $C_1$- to $C_4$-alkylsulfinyl group or a carboxyl group), a hydroxy group, a $C_1$- to $C_{16}$-alkoxy group (whose alkyl moiety is optionally substituted with a $C_2$- to $C_7$-alkoxycarbonyl group, a carboxyl group, a di-$C_1$- to $C_4$-alkylamino group, an N-$C_1$- to $C_4$-alkyl-substituted piperazino group, a hydroxy group or a nitroxy group), a $C_2$- to $C_7$-alkylcarbonyloxy group, a methylenedioxy group, a $C_2$- to $C_7$-alkoxycarbonyl group, a carboxyl group, a cyano group, a $C_1$- to $C_4$-alkylthio group or a $C_1$- to $C_4$-alkylsulfinyl group; $R^3$ and $R^4$, which may be the same or different, independently represents a $C_1$- to $C_6$-alkyl group or $R^3$ and $R^4$ are combined together to form a $C_2$- to $C_4$-alkylene group optionally intervened by a nitrogen atom; X represents an oxygen atom, a sulfur atom or a methylene group; l represents an integer of 1 to 3; and m and n represent 0 or an integer of 1. The present invention also relates to processes for producing the ketenedithioacetal derivative and to a pharmaceutical composition containing the derivative as an active ingredient, more particularly to an anti-hyperlipemic and anti-arteriosclerotic composition.

DESCRIPTION OF THE PRIOR ART

Ketenedithioacetals represented by formula:

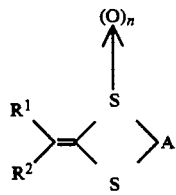

[wherein $R_1$ is an aryl or a heteroaryl; $R_2$ is hydrogen, a hydrocarbon group which may optionally be substituted, a heteroaryl, an acyl or a sulfo shown by formula: $-S(O)_mR_a$ (wherein m is 0, 1 or 2 and $R_a$ is a hydrocarbon group which is optionally substituted) or an optionally functionally modified sulfo; A is a bivalent aliphatic hydrocarbon group which may optionally be substituted; and n is 0 or 1], are described in Japanese Patent Application KOKAI (the term "KOKAI" is used herein to refer to an unexamined application which was laid open to public inspection) No. 59-16887; it is also mentioned therein that these compounds are useful as anti-cholesterol agents. However, no specific experimental data is disclosed. A variety of combinations of substituents are considered based on the claim definitions but none of them is suggestive of the present invention.

As a result of extensive studies, the present inventors have found that the ketenedithioacetal derivatives represented by general formula (I) have a more potent hypolipidemic and anti-arteriosclerotic effect than those described in Japanese Patent Application KOKAI No. 59-16887 and have accomplished the present invention.

SUMMARY OF THE INVENTION

An object of the present invention is to provide ketenedithioacetal derivatives and pharmaceutically acceptable salts thereof which exhibit a potent hypolipidemic and anti-arteriosclerotic activity.

Another object of the present invention is to provide processes for producing the ketenedithioacetal derivatives useful as hypolipidemic and anti-arteriosclerotic agents.

A further object of the present invention is to provide hypolipidemic and anti-arteriosclerotic compositions containing the ketenedithioacetal derivatives as active ingredient that are low-toxic and effective for prophylaxis and treatment of hyperlipemia and arteriosclerosis.

According to the present invention, the ketenedithioacetal derivatives represented by general formula (I) described above are provided.

DESCRIPTION OF THE PREFERRED EMBODIMENTS

In the general formula (I) described above, $R^1$ preferably represents an alkyl group having 1 to 4 carbon atoms such as methyl, ethyl, isopropyl, n-butyl, etc.; $R^2$ preferably represents a halogen atom such as fluorine atom, chlorine atom, bromine atom, etc.; an alkyl group having 1 to 4 carbon atoms such as methyl, ethyl, n-propyl, t-butyl, etc.; hydroxy group and an alkoxy group such as methoxy, ethoxy, n-propoxy, isopropoxy, n-hexyloxy, n-octyloxy, n-dodecyloxy, carboxymethoxy, 3-carboxypropoxy, 4-carboxy-4-methylpentyloxy, 2-carboxy-2-propoxy, 2-dimethylaminoethoxy, 3-dimethylaminopropoxy or 4-methylmorpholinopropoxy which may optionally be substituted with carboxyl group, an alkoxycarbonyl group, a substituted amino group or a cyclic amino group. $R^3$ and $R^4$ are combined together to form an alkylene group preferably having 2 or 3 carbon atoms. l preferably represents an integer of 1 and, m and n preferably represent 0.

Specific and preferred examples of the ketenedithioacetal derivatives are 2-[1-{4-(4-methoxyphenoxyphenyl)}ethan-1-ylidene]-1,3-dithiane, 2-[1-{4-(4-n-propoxyphenoxyphenyl)}ethan-1-ylidene]-1,3-dithiane, 2-[1-[4-(4-i-propoxyphenoxyphenyl)}ethan-1-ylidene]-1,3-dithiane, 2-[1-{4-(4-(3-dimethylaminopropoxy)-phenoxyphenyl)}ethan-1-ylidene]-1,3-dithiane, 2-[1-(4-phenoxyphenyl)}propan-1-ylidene]-1,3-dithiane, 2-[1-{4-(4-acetoxyphenoxyphenyl)}propan-1-ylidene]-1,3-dithiane, 2-[1-{4-(4-n-propoxyphenoxyphenyl)}propan-1-ylidene]-1,3-dithian, 2-[1-{4-(3-methyl-4-hydroxyphenoxy)phenyl}ethan-1-ylidene]-1,3-dithiane, 2-[1-{4-

(3,5-dimethyl-4-hydroxyphenoxy)phenyl}ethan-1-ylidene]-1,3-dithiane, 4-[4-{1-(1,3-dithian-2-ylidene)ethan-1-yl}phenoxy]phenoxyacetic acid, 4-[4-{1-(1,3-dithian-2-ylidene)ethan-1-yl}phenoxy]phenylacetic acid, 2-[1-{4-(4-hydroxyphenoxy)phenyl}ethan-1-ylidene]-1,3-dithiane, 2-[1-{4-(3-hydroxyphenoxy)phenyl}ethan-1-ylidene]-1,3-dithiane, 2-[1-[4-(3-methoxyphenoxy)phenyl}ethan-1-ylidene]-1,3-dithiane, ethyl 4-[4-[1-(1,3-dithian-2-ylidene)ethan-1-yl}phenoxy]benzoate, Ethyl 4-[4-{1-(1,3-dithian-2-ylidene)ethan-1-yl}phenoxy]phenylacetate, 2-[1-{4-(3-methyl-4-hydroxyphenoxy)phenyl}ethan-1-ylidene]-1,3-dithiane, 2-[1-{4 (3,5-dimethyl-4-hydroxyphenoxy)phenyl}ethan-1-ylidene]-1,3-dithiane, 4-[4-{1-(1,3-dithian-2-ylidene)ethan-1-yl}phenoxy]-phenoxybutyric - acid and 2-[1-{4-(4-fluorophenoxy)-phenyl}ethan-1-ylidene]-1,3-dithiane.

The compounds represented by general formula (I) can be produced by Process A or Process B.

Process A:

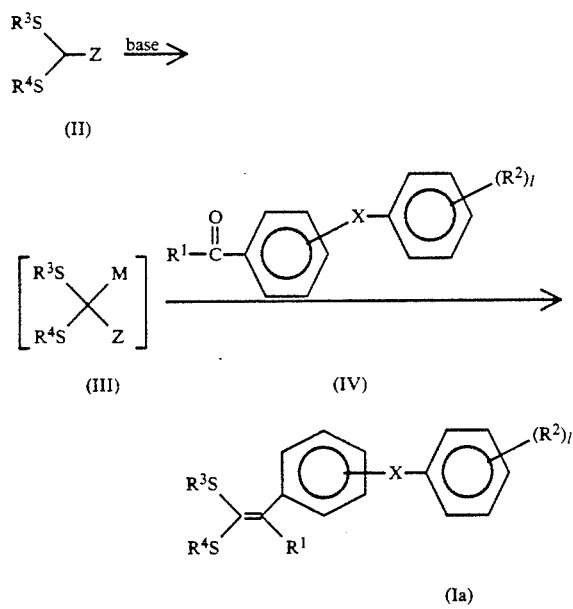

(Ia)

wherein $R^1$, $R^2$, $R^3$, $R^4$, X and l have the same meanings as described above; M represents an alkali metal atom; and Z represents trimethylsilyl group, triphenylsilyl group, a dialkoxyphosphoryl group, tributylstannyl group or chlorotriphenylphosphonium group.

The compound represented by general formula (Ia) can be obtained by reacting the compound represented by general formula (II) with a base in an anhydrous inert solvent under cooling, for example, at temperatures of from −78° C. to 0° C. to convert into the alkali metal salt represented by general formula (III), then adding the compound represented by general formula (IV) thereto under cooling, for example, at temperatures of from −78° C. to 0° C. and then reacting the mixture under mild conditions, for example, at 0° to 50° C.

As the solvent used in this reaction, non-aqueous inert solvents are preferred and examples include hydrocarbons such as n-hexane, cyclohexane, isooctane, benzene, etc.; ethers such as diethyl ether, dioxane, tetrahydrofuran, dimethoxymethane, etc.

As the base, there are n-butyl lithium, s-butyl lithium, phenyl lithium, lithium diisopropylamide, lithium dicyclohexaylamide, lithium hexamethyldisilazane, sodium hydride and potassium hydride. The base is used generally in an equimolar amount based on the compound represented by general formula (II).

The reactants in the reaction may be used in an equimolar ratio since the reaction is equimolar one but either one of the reactants may be used in an excess amount.

The reaction time varies depending upon reaction temperature and reaction scale but is generally chosen from a range of 30 minutes to 48 hours.

Process B:

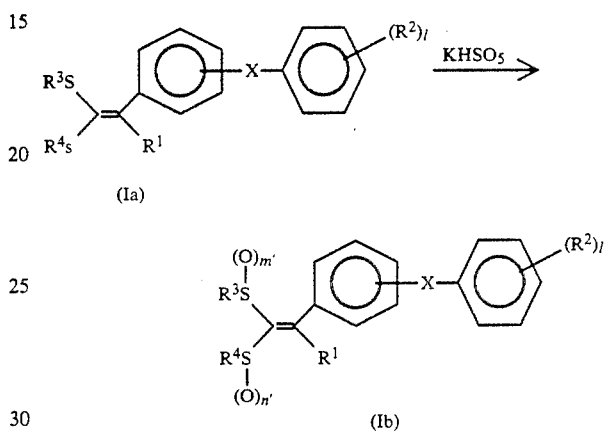

wherein $R^1$, $R^2$, $R^3$, $R^4$, X and l have the same meanings as described above; m' and n' represent 0 or an integer of 1, provided that both m' and n' are not 0 simultaneously.

The compound represented by general formula (Ib) can be obtained by oxidizing the compound represented by general formula (Ia) with an appropriate oxidizing agent, for example, oxon, in an inert solvent.

The solvent used in this reaction may be any solvent as far as it does not interfere the reaction and examples include water; alcohols such as methanol, ethanol, isopropyl alcohol, etc.; ethers such as tetrahydrofuran, dioxane, dimethoxymethane, etc.

In the case of performing the reaction, the reaction temperature is chosen from a range of 0 to 40° C.; the reaction time varies depending upon reaction temperature and reaction scale but is generally chosen from a range of 1 to 48 hours. A molar ratio of the reactants is chosen from a range of an equimole to 2-fold moles depending upon purpose, since the system contains two sulfurs which may undergo oxidation.

The product obtained by Process A or Process B can be isolated in a conventional manner and further purified by means of recrystallization, column chromatography, etc.

Further, the salt of the compounds of general formula (I) can be obtained by reacting the compound of general formula (I) with a suitable organic or inorganic acid such as citric acid, maleic acid, hydrochloric acid and the like.

Next, representative examples of the compounds represented by general formula (I) are shown in Table 1 but the present invention is not deemed to be limited thereto.

General formula (I):

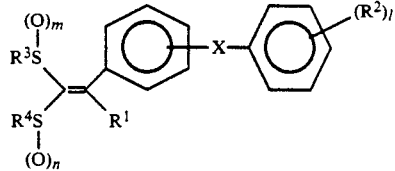

TABLE 1

| Compound No. | $R^1$ | $-X-\phantom{}\bigcirc(R^2)_l$ | $R^3$ | $R^4$ | m | n | Physical Properties [melting point or refractive index] ($n_D$ °C.) |
|---|---|---|---|---|---|---|---|
| 1 | CH$_3$ | 4-O—⬡ | | —(CH$_2$)$_3$— | 0 | 0 | $n_D^{16.5}$ 1.6486 |
| 2 | CH$_3$ | 4-O—⬡—F | | —(CH$_2$)$_3$— | 0 | 0 | paste |
| 3 | CH—4-OCH—⬡—Cl | —(CH$_2$)$_3$— | | | 0 | 0 | paste |
| 4 | CH$_3$ | 4-O—⬡—CH$_3$ | | —(CH$_2$)$_3$— | 0 | 0 | m.p. 69.5–71.0° C. |
| 5 | CH$_3$ | 4-O—⬡—OH | | —(CH$_2$)$_3$— | 0 | 0 | m.p. 84.5–87.5° C. |
| 6 | CH$_3$ | 4-O—⬡—OCH$_3$ | | —(CH$_2$)$_3$— | 0 | 0 | m.p. 85.0–86.0° C. |
| 7 | CH$_3$ | 4-O—⬡(OCH$_3$)(OCH$_3$) | | —(CH$_2$)$_3$— | 0 | 0 | m.p. 73.5–75.5° C. |
| 8 | CH$_3$ | 4-O—⬡(OCH$_3$)(OCH$_3$)(OCH$_3$) | | —(CH$_2$)$_3$— | 0 | 0 | m.p. 86.0–87.0° C. |
| 9 | C$_2$H$_5$ | 4-O—⬡ | | —(CH$_2$)$_3$— | 0 | 0 | m.p. 53.0–54.0° C. |
| 10 | C$_2$H$_5$ | 4-O—⬡—OCH$_3$ | | —(CH$_2$)$_3$— | 0 | 0 | m.p. 64.0–65.0° C. |

TABLE 1-continued

| Compound No. | R¹ | −X−⬡−(R²)ₗ | R³ | R⁴ | m | n | Physical Properties [melting point or refractive index] (n_D°C.) |
|---|---|---|---|---|---|---|---|
| 11 | C₂H₅ | 4-O−⬡−OC₂H₅ | | ₊(CH₂)₃ | 0 | 0 | m.p. 58.5–60.0° C. |
| 12 | i-C₃H₇ | 4-O−⬡ | | ₊(CH₂)₃ | 0 | 0 | m.p. 63.0–63.5° C. |
| 13 | n-C₄H₉ | 4-O−⬡ | | ₊(CH₂)₃ | 0 | 0 | n_D^{24.0} 1.6220 |
| 14 | −CH₂CH₂COCH₃ ‖ O | 4-O−⬡ | | ₊(CH₂)₃ | 0 | 0 | m.p. 95.0–96.0° C. |
| 15 | −CH₂CH₂COCH₃ ‖ O | 4-O−⬡−OCH₃ | | ₊(CH₂)₃ | 0 | 0 | m.p. 43.5–46.0° C. |
| 16 | −CH₂CH₂COH ‖ O | 4-O−⬡ | | ₊(CH₂)₃ | 0 | 0 | m.p. 154.5–155.0° C. |
| 17 | −CH₂CH₂COH ‖ O | 4-O−⬡−OCH₃ | | ₊(CH₂)₃ | 0 | 0 | m.p. 123.0–125.0° C. |
| 18 | CH₃ | 4-O−⬡−OCH₃ | | ₊(CH₂)₂ | 0 | 0 | m.p. 84.0–85.0° C. |
| 19 | C₂H₅ | 4-O−⬡ | | ₊(CH₂)₂ | 0 | 0 | paste |
| 20 | CH₃ | 4-O−⬡−OCH₃ | | ₊(CH₂)₂ | 0 | 0 | m.p. 56.0–57.0° C. |
| 21 | CH₃ | 4-O−⬡ | | CH₃ \| −CH₂NCH₂− | 0 | 0 | m.p. 93.5–94.5° C. |
| 22 | C₂H₅ | 4-O−⬡ | | CH₃ \| −CH₂NCH₂− | 0 | 0 | m.p. 96.0–96.5° C. |
| 23 | CH₃ | 4-CH₂−⬡ | | ₊(CH₂)₃ | 0 | 0 | n_D^{25.0} 1.6514 |

TABLE 1-continued

| Compound No. | $R^1$ | $-X-$⟨phenyl ring with $(R^2)_l$⟩ | $R^3$ | $R^4$ | m | n | Physical Properties [melting point or refractive index] ($n_D^{°C}$) |
|---|---|---|---|---|---|---|---|
| 24 | $C_2H_5$ | 4-$CH_2$–⟨phenyl⟩ | | $(CH_2)_3$ | 0 | 0 | m.p. 46.5–48.0° C. |
| 25 | $C_2H_5$ | 4-$CH_2$–⟨phenyl⟩–F | | $(CH_2)_3$ | 0 | 0 | m.p. 40.0–43.0° C. |
| 26 | $CH_3$ | 4-O–⟨phenyl⟩–$OCH_3$ | | $(CH_2)_3$ | 1 | 0 | m.p. 136.0–138.0° C. |
| 27 | $CH_3$ | 4-O–⟨phenyl⟩–$OCH_3$ | | $(CH_2)_3$ | 0 | 1 | paste |
| 28 | $CH_3$ | 4-O–⟨phenyl⟩–$OC_3H_7$-n | | $(CH_2)_3$ | 0 | 0 | $n_D^{10.5}$ 1.6305 |
| 29 | $CH_3$ | 4-O–⟨phenyl⟩–$OC_3H_7$-i | | $(CH_2)_3$ | 0 | 0 | $n_D^{10.5}$ 1.6324 |
| 30 | $CH_3$ | 4-O–⟨phenyl⟩–$OC_6H_{13}$-n | | $(CH_2)_3$ | 0 | 0 | $n_D^{11.5}$ 1.6091 |
| 31 | $CH_3$ | 4-O–⟨phenyl⟩–$OC_8H_{17}$-n | | $(CH_2)_3$ | 0 | 0 | $n_D^{24.0}$ 1.5845 |
| 32 | $CH_3$ | 4-O–⟨phenyl⟩–$OC_{12}H_{25}$-n | | $(CH_2)_3$ | 0 | 0 | m.p. 64.0–65.0° C. |
| 33 | $CH_3$ | 4-O–⟨phenyl⟩–$OCCH_3$ (C=O) | | $(CH_2)_3$ | 0 | 0 | $n_D^{23.0}$ 1.6290 |
| 34 | $CH_3$ | 4-O–⟨phenyl⟩–$OCC_2H_5$ (C=O) | | $(CH_2)_3$ | 0 | 0 | $n_D^{23.0}$ 1.6228 |
| 35 | $CH_3$ | 4-O–⟨phenyl⟩–$OCC_4H_9$-t (C=O) | | $(CH_2)_3$ | 0 | 0 | $n_D^{25.5}$ 1.5930 |

TABLE 1-continued

| Compound No. | R¹ | —X—⌬—(R²)ₗ | R³ | R⁴ | m | n | Physical Properties [melting point or refractive index] ($n_D^{°C}$) |
|---|---|---|---|---|---|---|---|
| 36 | CH₃ | 4-O—⌬—OCH₂COOC₂H₅ | | ₊(CH₂)₃̄ | 0 | 0 | $n_D^{13.0}$ 1.6149 |
| 37 | CH₃ | 4-O—⌬—OCH₂COOH | | ₊(CH₂)₃̄ | 0 | 0 | m.p. 129–131.5° C. |
| 38 | CH₃ | 4-O—⌬—OC(CH₃)₂COOH | | ₊(CH₂)₃̄ | 0 | 0 | paste |
| 39 | CH₃ | 4-O—⌬—OCH₂CH₂CH₂COOH | | ₊(CH₂)₃̄ | 0 | 0 | m.p. 125–125.5° C. |
| 40 | CH₃ | 4-O—⌬—OCH₂CH₂CH₂C(CH₃)₂COOH | | ₊(CH₂)₃̄ | 0 | 0 | $n_D^{24.5}$ 1.5677 |
| 41 | CH₃ | 4-O—⌬—OCH₂CH₂N(CH₃)₂ | | ₊(CH₂)₃̄ | 0 | 0 | $n_D^{25.0}$ 1.6037 |
| 42 | CH₃ | 4-O—⌬—OCH₂CH₂CH₂N(CH₃)₂ | | ₊(CH₂)₃̄ | 0 | 0 | $n_D^{24.5}$ 1.6102 |
| 43 | CH₃ | 4-O—⌬—OCH₂CH₂N(piperazine)NCH₃ | | ₊(CH₂)₃̄ | 0 | 0 | $n_D^{28.5}$ 1.6069 |
| 44 | CH₃ | 4-O—⌬—OCH₂CH₂CH₂N(piperazine)NCH₃ | | ₊(CH₂)₃̄ | 0 | 0 | m.p. 187.0–188° C. (maleate) |
| 45 | CH₃ | 4-O—⌬—OCH₂CH₂CH₂N(piperazine)NCH₃ | | ₊(CH₂)₃̄ | 0 | 0 | m.p. 118.0–120.0° C. (citrate) |
| 46 | CH₃ | 4-O—⌬—OCH₂CH₂CH₂ONO₂ | | ₊(CH₂)₃̄ | 0 | 0 | $n_D^{24.5}$ 1.6067 |
| 47 | CH₃ | 4-O—⌬—OCH₂CH(OH)CH₂OH | | ₊(CH₂)₃̄ | 0 | 0 | paste |

TABLE 1-continued

| Compound No. | $R^1$ | $-X-\phenyl(R^2)_l$ | $R^3$ | $R^4$ | m | n | Physical Properties [melting point or refractive index] $(n_D^{°C.})$ |
|---|---|---|---|---|---|---|---|
| 48 | $C_2H_5$ | 4-O—⌬—$OC_3H_7$-n | | $(CH_2)_3$ | 0 | 0 | $n_D^{23.0}$ 1.6162 |
| 49 | $C_2H_5$ | 4-O—⌬—$OCH_2COOC_2H_5$ | | $(CH_2)_3$ | 0 | 0 | m.p. 88.0–89.0° C. |
| 50 | $C_2H_5$ | 4-O—⌬—$OCH_2COOH$ | | $(CH_2)_3$ | 0 | 0 | m.p. 153.0–155.0° C. |
| 51 | $C_2H_5$ | 4-O—⌬—$OCCH_3$ (C=O) | | $(CH_2)_3$ | 0 | 0 | m.p. 63.0–64.5° C. |
| 52 | $C_2H_5$ | 4-O—⌬—$OCH_2CH_2CH_2N$⟨piperazine⟩$NCH_3$ | | $(CH_2)_3$ | 0 | 0 | $n_D^{28.5}$ 1.5982 |
| 53 | $C_2H_5$ | 4-O—⌬—$OCH_2CH_2CH_2N$⟨piperazine⟩$NCH_3$ | | $(CH_2)_3$ | 0 | 0 | m.p. 184.0–185.0° C. (maleate) |
| 54 | $C_2H_5$ | 4-O—⌬—$OCH_2CH_2CH_2N$⟨piperazine⟩$NCH_3$ | | $(CH_2)_3$ | 0 | 0 | m.p. 110.0–112.0° C. (citrate) |
| 55 | $C_2H_5$ | 4-O—⌬—OH | | $(CH_2)_3$ | 0 | 0 | m.p. 98.0–100.0° C. |
| 56 | $CH_3$ | 4-O—⌬($CH_3O$-) | | $(CH_2)_3$ | 0 | 0 | m.p. 101.0–102.5° C. |
| 57 | $CH_3$ | 4-O—⌬—OH | | $(CH_2)_3$ | 0 | 0 | $n_D^{25.5}$ 1.6421 |
| 58 | $C_2H_5$ | 4-O—⌬—OH | | $(CH_2)_3$ | 0 | 0 | $n_D^{18.5}$ 1.6540 |
| 59 | $CH_3$ | 4-O—⌬—$OCH_3$ | | $(CH_2)_3$ | 0 | 0 | $n_D^{24.7}$ 1.6398 |

TABLE 1-continued $$-X-\underset{}{\underset{}{\bigcirc}}(R^2)_l$$

| Compound No. | $R^1$ | (aryl group) | $R^3$ | $R^4$ | m | n | Physical Properties [melting point or refractive index] $(n_D \cdot °C.)$ |
|---|---|---|---|---|---|---|---|
| 60 | $C_2H_5$ | 4-O-phenyl-3-OCH₃ | | $(CH_2)_3$ | 0 | 0 | $n_D^{25.5}$ 1.6427 |
| 61 | $CH_3$ | 4-O-phenyl-2,3-(OH)₂ | | $(CH_2)_3$ | 0 | 0 | m.p. 127.0–128.5° C. |
| 62 | $CH_3$ | 4-O-phenyl-2,5-(OH)₂ | | $(CH_2)_3$ | 0 | 0 | $n_D^{17.5}$ 1.5883 |
| 63 | $CH_3$ | 4-O-phenyl-2-CH₃-3-OH | | $(CH_2)_3$ | 0 | 0 | $n_D^{25.0}$ 1.6518 |
| 64 | $CH_3$ | 4-O-phenyl-2-CH₃-3-OCH₃ | | $(CH_2)_3$ | 0 | 0 | paste |
| 65 | $CH_3$ | 4-O-phenyl-2-C₄H₉-t-3-OH | | $(CH_2)_3$ | 0 | 0 | $n_D^{17.5}$ 1.5838 |
| 66 | $CH_3$ | 4-O-phenyl-2-CH₃-3-OH-5-CH₃ | | $(CH_2)_3$ | 0 | 0 | $n_D^{25.0}$ 1.6010 |
| 67 | $C_2H_5$ | 4-O-phenyl-2-CH₃-3-OH-5-CH₃ | | $(CH_2)_3$ | 0 | 0 | m.p. 96.0–97.0° C. |
| 68 | $CH_3$ | 4-O-phenyl-2-CH₃-3-OCH₃-5-CH₃ | | $(CH_2)_3$ | 0 | 0 | $n_D^{25.0}$ 1.6235 |

TABLE 1-continued

| Compound No. | R¹ | −X−⟨phenyl⟩−(R²)ₗ | R³ | R⁴ | m | n | Physical Properties [melting point or refractive index] ($n_D^{\circ C}$) |
|---|---|---|---|---|---|---|---|
| 69 | CH₃ |  4-O-phenyl-O-CH₂-O (methylenedioxy) | | -(CH₂)₃- | 0 | 0 | m.p. 73.5–76.0° C. |
| 70 | CH₃ | 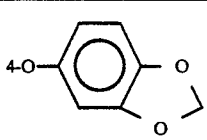 4-O-phenyl with CH₂S(→O)CH₃ and OH | | -(CH₂)₃- | 0 | 0 | m.p. 169.0–170.0° C. |
| 71 | C₂H₅ | 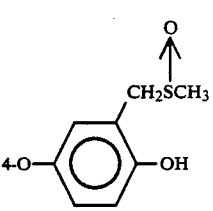 4-S-phenyl with CH₃, OH, CH₃ | | -(CH₂)₃- | 0 | 0 | m.p. 109.0–109.5° C. |
| 72 | C₂H₅ | 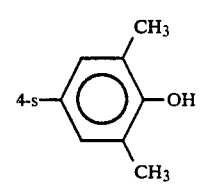 4-S-phenyl with C₄H₉-t, OCH₃, C₄H₉-t | | -(CH₂)₃- | 0 | 0 | m.p. 155.0–156.5° C. |
| 73 | C₂H₅ | 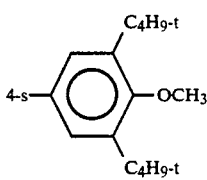 4-CH₂-phenyl with C₄H₉-t, OH, C₄H₉-t | | -(CH₂)₃- | 0 | 0 | m.p. 96.0–97.0° C. |
| 74 | CH₃ | 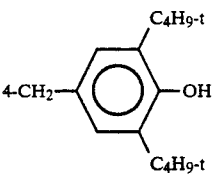 4-O-phenyl-COOC₂H₅ | | -(CH₂)₃- | 0 | 0 | m.p. 57.0–58.0° C. |
| 75 | CH₃ | 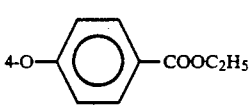 4-O-phenyl-COOH | | -(CH₂)₃- | 0 | 0 | m.p. 203–204.5° C. |
| 76 | CH₃ | 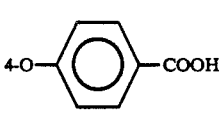 4-O-phenyl-CN | | -(CH₂)₃- | 0 | 0 | m.p. 119.0–120.5° C. |
| 77 | CH₃ | 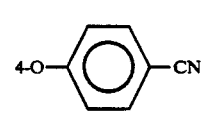 4-O-phenyl-CH₂COOC₂H₅ | | -(CH₂)₃- | 0 | 0 | $n_D^{21.5}$ 1.6200 |
| 78 | CH₃ | 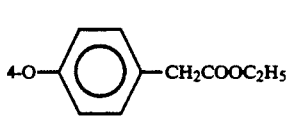 4-O-phenyl-CH₂COOH | | -(CH₂)₃- | 0 | 0 | m.p. 124.0–125.5° C. |

TABLE 1-continued

| Compound No. | R¹ | -X-⌬-(R²)ₗ | R³ | R⁴ | m | n | Physical Properties [melting point or refractive index] ($n_D^{°C.}$) |
|---|---|---|---|---|---|---|---|
| 79 | CH₃ | 4-O-⌬-SCH₃ | | -(CH₂)₃- | 0 | 0 | m.p. 70.5–71.5° C. |
| 80 | CH₃ | 4-O-⌬-S(→O)-CH₃ | | -(CH₂)₃- | 0 | 0 | m.p. 131.5–132.5° C. |
| 81 | CH₃ | 4-S-⌬-OCH₃ | | -(CH₂)₃- | 0 | 0 | $n_D^{18.5}$ 1.6842 |
| 82 | CH₃ | 4-S-⌬-OH | | -(CH₂)₃- | 0 | 0 | m.p. 113.0–114.0° C. |
| 83 | CH₃ | 4-S-⌬(2,6-(CH₃)₂)-OH | | -(CH₂)₃- | 0 | 0 | $n_D^{23.0}$ 1.6710 |
| 84 | CH₃ | 4-S-⌬(2,6-(C₄H₉-t)₂)-OH | | -(CH₂)₃- | 0 | 0 | m.p. 149.0–150.0° C. |
| 85 | CH₃ | 4-S-⌬(2,6-(C₄H₉-t)₂)-OCOCH₃ | | -(CH₂)₃- | 0 | 0 | m.p. 119.5–120.5° C. |
| 86 | CH₃ | 4-CH₂-⌬(2,6-(C₄H₉-t)₂)-OH | | -(CH₂)₃- | 0 | 0 | $n_D^{23.0}$ 1.5763 |
| 87 | -CH₂CH₂CH₂COOCH₃ | 4-O-⌬ | | -(CH₂)₃- | 0 | 0 | paste |
| 88 | -CH₂CH₂CH₂COOH | 4-O-⌬ | | -(CH₂)₃- | 0 | 0 | m.p. 68.5–70.5° C. |

TABLE 1-continued

| Compound No | R¹ | —X—⌬—(R²)ₗ | R³ | R⁴ | m | n | Physical Properties [melting point or refractive index] ($n_D^{°C}$) |
|---|---|---|---|---|---|---|---|
| 89 | —CH₂N(CH₃)₂ | 4-O—⌬—OCH₃ | ⁺(CH₂)₃ | | 0 | 0 | m.p. 92.0–93.0° C. |
| 90 | —CH₂CH₂N(CH₃)₂ | 4-O—⌬—OCH₃ | ⁺(CH₂)₃ | | 0 | 0 | m.p. 64.0–65.0° C. |
| 91 | C₂H₅ | 4-S—⌬(CH₃)(CH₃)—OH | ⁺(CH₂)₂ | | 0 | 0 | $n_D^{23.0}$ 1.6622 |
| 92 | C₂H₅ | 4-O—⌬—OH | (—CH₂)₂ | | 0 | 0 | $n_D^{22.5}$ 1.5795 |
| 93 | CH₃ | 4-S—⌬(C₄H₉-t)(C₄H₉-t)—OH | C₂H₅ | C₂H₅ | 0 | 0 | m.p. 126.0–127.0° C. |
| 94 | CH₃ | 4-O—⌬ | CH₃ | CH₃ | 0 | 0 | $n_D^{19.5}$ 1.5740 |
| 95 | C₂H₅ | 4-O—⌬ | CH₃ | CH₃ | 0 | 0 | $n_D^{19.5}$ 1.6318 |
| 96 | C₂H₅ | 4-O—⌬ | C₂H₅ | C₂H₅ | 0 | 0 | $n_D^{19.5}$ 1.5988 |
| 97 | C₂H₅ | 4-O—⌬—OCH₃ | C₂H₅ | C₂H₅ | 0 | 0 | $n_D^{27.5}$ 1.6039 |
| 98 | CH₃ | 4-O—⌬ | n-C₄H₉ | n-C₄H₉ | 0 | 0 | $n_D^{25}$ 1.5805 |
| 99 | C₂H₅ | 4-O—⌬ | n-C₄H₉ | n-C₄H₉ | 0 | 0 | $n_D^{25}$ 1.5709 |
| 100 | C₂H₅ | 4-O—⌬—OH | C₂H₅ | C₂H₅ | 0 | 0 | $n_D^{23.5}$ 1.6011 |

TABLE 1-continued

| Compound No. | $R^1$ | $-X-\phantom{}$⟨phenyl⟩$-(R^2)_l$ | $R^3$ | $R^4$ | m | n | Physical Properties [melting point or refractive index] $(n_D\,^\circ C.)$ |
|---|---|---|---|---|---|---|---|
| 101 | $C_2H_5$ | 4-O—⟨phenyl⟩—$OC_2H_5$ | $C_2H_5$ | $C_2H_5$ | 0 | 0 | $n_D^{23.5}$ 1.5898 |
| 102 | $C_2H_5$ | 4-O—⟨phenyl⟩—$OC_3H_7$-n | $C_2H_5$ | $C_2H_5$ | 0 | 0 | $n_D^{23.0}$ 1.5835 |
| 103 | $C_2H_5$ | 4-O—⟨phenyl⟩—$OC_3H_7$-i | $C_2H_5$ | $C_2H_5$ | 0 | 0 | $n_D^{22.5}$ 1.5840 |

Next, NMR spectra data of the compounds, whose physical properties are expressed in Table 1 in the term "paste" are shown below.

| Compounds No. | NMR δ $CDCl_3$ TMS (PPM) |
|---|---|
| 2 | 1.9~2.3 (2H, m), 2.2 (3H, s), 2.7~3.15 (4H, m), 6.7~7.35 (8H, m) |
| 3 | 1.8~2.3 (2H, m), 2.2 (3H, s), 2.7~3.2 (4H, m), 6.8~7.45 (8H, m) |
| 20 | 1.00 (3H, t), 2.50 (2H, d), 3.20~3.50 (4H, m), 6.67~7.50 (9H, m) |
| 27 | 1.7~2.13 (1H, m), 2.43 (3H, s), 2.3~3.6 (5H, m), 3.8 (3H, s), 6.6~7.33 (8H, m) |
| 38 | 1.58 (6H, s), 2.17 (3H, s), 1.90~2.28 (2H, m), 2.58~3.11 (4H, m), 6.48 (1H, br), 5.73~7.27 (8H, m) |
| 47 | 1.6~3.3 (2H, br), 1.95~2.4 (2H, m), 2.17 (3H, s), 2.6~3.2 (4H, m), 3.5~4.4 (5H, m), 6.7~7.3 (8H, m) |
| 64 | 1.83~2.37 (2H, m), 2.2 (6H, s), 2.63~3.13 (4H, m), 3.8 (3H, s), 6.6~7.27 (7H, m) |
| 87 | 1.3~1.9 (2H, m), 1.95~2.55 (4H, m), 2.6~3.17 (6H, m), 3.63 (3H, s), 6.75~7.57 (9H, m) |

The ketenedithioacetal derivatives represented by general formula (I) have such a low toxicity that even when these compounds are administered to rats in a dose of 300 mg/kg/day for consecutive 2 weeks, the rats neither show toxic symptoms nor die.

The compounds represented by general formula (I) are useful as drugs for curing arteriosclerosis and hyperlipidemia. For example, it is known that hyperlipidemia can be caused in an experimental animal by giving a feed rich of cholesterol, neutral fat, etc., and it was found that some of the compounds represented by general formula (I) showed marked cholesterol and triglyceride reducing effects in the animal suffering from experimental hyperlipidemia when administered orally or parenterally. Therefore, these compounds are useful as hypolipidemic agents. Furthermore, by virtue of these pharmacological effects, the compounds are useful also in preventing cerebral apoplexy and myocardial infarction caused by hyperlipidemia.

Arteriosclerosis, in particular, atherosclerosis is caused by deposition of lipid on arterial wall which results in hyperplasia and sclerosis.

Arteriosclerosis obstructs blood flow and inhibits the supply of oxygen to tissues. Particularly in brain or heart, it is known as the so-called "ischemic pathosis", namely, a main dangerous factor of cerebral infarction and myocardial infarction. In addition, arteriosclerosis reduces the flexibility of artery and causes cerebral hemorrhage. Therefore, the blood lipid reducing effect of the compounds of this invention is effective also in preventing arteriosclerosis, and hence cerebral apoplexy.

Moreover, the compounds of this invention were found to have the effect of reducing cholesterol in blood by inhibition of cholesterol absorption in intestine and depression of cholesterol synthesis and promotion of cholesterol excretion in liver.

Accordingly, the term "drugs for curing hyperlipidemia" used in the present specification means drugs for curing hyperlipidemia and preventing and/or curing various diseases caused thereby, by utilizing the pharmacological effects described above.

The compounds represented by general formula (I) can be used as they are as drugs for curing hyperlipidemia and arteriosclerosis. It is also possible to formulate them into mixtures with pharmaceutically acceptable diluents and/or other pharmacologically active ingredients according to pharmaceutical custom. Furthermore, they can be formulated also into dosage unit forms. Forms which they can have as drugs include powder, granules, tablets, dragees, capsules, pills, suspensions, solutions, emulsions, ampoules, injections, isotonic solutions, etc.

Formulation of the compound of this invention into a medicinal composition includes an embodiment in which the compound represented by general formula (I) is incorporated into the composition in the form of a mixture with pharmaceutically acceptable diluents. The term "diluents" used herein means materials other than the compound represented by general formula (I). The diluents may be any of solids, semisolids, liquids and ingestible capsules and include various materials, for example, excipients, extenders, binders, wetting agents, disintegrators, surfactants, lubricants, dispersants, buffers, taste-improver, odour-reducing agents, coloring matters, perfumes, preservatives, dissolution assistance, solvents, coatings, frostings, etc. But the diluents are not limited thereto. These materials are used alone or as a mixture thereof. Such pharmaceutically acceptable diluents are used as a mixture with other pharmacologically active ingredients in some cases.

A medicinal composition using the compound of this invention may be produced by any known method. For example, the active ingredient is mixed with pharmaceutically acceptable diluents to yield, for instance, granules, and then the composition thus obtained is formed, for example, into tablets. When the medicinal composition is used as a parenteral drugs, it should be sterilized. If necessary, it should be made isotonic with regard to blood.

In this invention, since the compounds represented by above general formula (I) themselves are applicable as drugs for curing hyperlipidemia and arteriosclerosis, the active ingredient is contained in the composition usually in an amount of 0.01 to 100% (by weight).

When the compound of this invention is formulated into a preparation of dosage unit, individual pharmaceutical portions constituting said preparation may be either in different forms or in the same forms, and there are often employed, for example, forms such as tablets, granules, pills powder, dragees, capules, and ampoules.

The drugs for curing hyperlipidemia and arteriosclerosis according to this invention can be applied to human beings and animals in order to prevent and cure hyperlipidemia and arteriosclerosis, by a method which is conventional in the fields of such prevention and therapy. They are administered orally or parenterally. The oral administration includes sublingual administration. The parenteral administration includes administration by injection (including, for example, subcutaneous injection, intramuscular injection, intravenous injection, and drip).

The dose of the drugs of this invention is varied depending various factors such as animals or human beings of subject, its sensitivity, age, sex and body weight, the administration route, time and interval of administration, the condition of a disease, the physical condition of the subject, the properties of pharmaceutical preparation, the kind of preparation, the kind of active ingredient, etc.

Therefore, in some cases, a dose smaller than the minimum dose described below is sufficient, and in other cases, a dose larger than the maximum dose described below is required.

In the case of a high dose, administration in several times a day is preferred.

In order to obtain effective results for animals, the dose in terms of the active ingredient is advantageously 0.1 to 500 mg, preferably 0.1 to 30 mg per kg of body weight per day in the case of oral administration, while in the case of parenteral administration, it is advantageously 0.01 to 250 mg, preferably 0.1 to 25 mg per kg of body weight per day.

In order to obtain effective results for human beings, in consideration of sensitivity difference, safety, etc. on the basis of the effective dose for animals, the dose for human beings seems to be advantageously for example, in the following ranges: in the case of oral administration, 0.1 to 200 mg, preferably 0.5 to 50 mg per kg of body weight per day, and in the case of parenteral administration, 0.01 to 100 mg, preferably 0.1 to 25 mg per kg of body weight per day.

Next, several examples are shown below but the present invention is not deemed to be limited thereto.

EXAMPLE 1

2-{1-(4-Phenoxyphenyl)ethan-1-ylidene}-1,3-dithiane (Compound No. 1)

2-Trimethylsilyl-1,3-dithiane, 1.92 g, was dissolved in 20 ml of tetrahydrofuran and 6.3 ml of 1.6 mole hexane solution of n-butyl lithium was dropwise added to the solution in an argon flow under ice cooling. The mixture was stirred at the same temperature for 30 minutes. Then, a solution of 2.33 g of 4-phenoxyacetophenone in 10 ml of tetrahydrofuran was dropwise added under ice cooling followed by stirring at the same temperature for 30 minutes and at room temperature for an hour. After saturated sodium chloride aqueous solution was added, the mixture was extracted with chloroform. After drying the chloroform phase over magnesium sulfate, the solvent was distilled off under reduced pressure and the residue was purified by silica gel column chromatography (ethyl acetate : hexane = 1 : 10) to give 2.7 g of the oily product.

$N_D^{16.5}$ 1.6486, yield: 85.9%

EXAMPLE 2

2-[1-{4-(4-Hydroxyphenoxy)phenyl}ethan-1-ylidene]-1,3-dithiane (Compound No. 5)

2-Diethoxyphosphoryl-1,3-dithiane, 2.05 g, was dissolved in 35 ml of tetrahydrofuran and 5 ml of 1.6 mole hexane solution of n-butyl lithium was dropwise added to the solution in an argon flow at −65° C. The mixture was stirred at the same temperature for an hour. Then, 4.4 ml of a solution of 1.6 N n-butyl lithium in hexane and 4-(4-hydroxyphenoxy)acetone in 15 ml of tetrahydrofuran were dropwise added to the mixture at the same temperature. The reaction mixture was gradually warmed to room temperature overnight. This suspension was poured onto water. After the mixture was rendered acidic to pH of 2 with conc. hydrochloric acid, it was extracted with ethyl acetate. After drying the ethyl acetate phase over magnesium sulfate, the solvent was distilled off under reduced pressure and the residue was purified by silica gel column chromatography (ethyl acetate : hexane = 1 : 3) to give 0.98 g of the product.

m.p. 84.5°–14 87.5° C., yield: 42%

EXAMPLE 3

2-{1-(4-Phenoxyphenyl)propan-1-ylidene}-1,3-dithiane (Compound No. 9)

2-Diethoxyphosphoryl-1,3-dithiane, 4.18 g, was dissolved in 40 ml of tetrahydrofuran and 10.5 ml of 1.6 mole hexane solution of n-butyl lithium was dropwise added to the solution in an argon flow at −65° C. The mixture was stirred at the same temperature for an hour. Then, a solution of 36.2 g of 4-phenoxypropiophenone in 15 ml of tetrahydrofuran was dropwise added to the mixture at the same temperature. The reaction mixture was gradually warmed to room temperature overnight. This suspension was poured onto saturated sodium chloride aqueous solution followed by extraction with chloroform. After drying the chloroform phase over magnesium sulfate, the solvent was distilled off under reduced pressure and the residue was purified by silica gel column chromatography (chloroform : hexane = 1 : 1) to give 4.15 g of the product.

m.p. 53.0°–54.0° C., yield: 79%

EXAMPLE 4

2-{1-(4-Phenoxyphenyl)propan-1-ylidene}-1,3-dithiolan (Compound No. 19)

2-Diethoxyphosphoryl-1,3-dithiolan, 3.0 g, was dissolved in 30 ml of tetrahydrofuran and 7.75 ml of 1.6 mole hexane solution of n-butyl lithium was dropwise added to the solution in an argon flow at −65° C. The mixture was stirred at the same temperature for an hour. Then, a solution of 2.55 g of 4-phenoxypropiophenone in 9 ml of tetrahydrofuran was dropwise added to the mixture at the same temperature. The reaction mixture was gradually warmed to room temperature overnight. This suspension was poured onto saturated sodium chloride aqueous solution and the mixture was extracted with chloroform. After drying the chloroform phase over magnesium sulfate, the solvent was distilled off under reduced pressure and the residue was purified by silica gel column chromatography (chloroform : hexane =1 : 1) to give 2.60 g of the product.

paste, yield: 73%

EXAMPLE 5

Methyl 4-(1,3-dithian-2-ylidene)-4-(4-phenoxyphenyl)-butyrate (Compound No. 14)

2-Diethoxyphosphoryl-1,3-dithiane, 2.82 g, was dissolved in 30 ml of tetrahydrofuran and 7 ml of 1.6 mole hexane solution of n-butyl lithium was dropwise added to the solution in an argon flow at −65° C. The mixture was stirred at the same temperature for an hour. Then, a solution of 2.8 g of 4-(4-phenoxyphenyl)-4-oxobutyrate in 10 ml of tetrahydrofuran was dropwise added to the mixture at the same temperature. The reaction mixture was gradually warmed to room temperature overnight. This suspension was poured onto saturated sodium chloride aqueous solution followed by extraction with chloroform. After drying the chloroform phase over magnesium sulfate, the solvent was distilled off under reduced pressure and the residue was purified by silica gel column chromatography (chloroform : hexane =1 : 1) to give 2.33 g of the product.

m.p. 95°–96° C., yield: 61%

EXAMPLE 6

4-(1,3-Dithian-2-ylidene)-4-(4-phenoxyphenyl)butyric acid (Compound No. 16)

Methyl 4-(1,3-dithian-2-ylidene)-4-(4-phenoxyphenyl)-butyrate, 1.29 g, was dissolved in a solvent mixture of 30 ml of tetrahydrofuran and 30 ml of ethanol and, 10 ml of 1 N sodium hydroxide aqueous solution was added to the solution followed by stirring at room temperature for 2 hours. Water was added to the reaction mixture. After washing with ethyl acetate, the aqueous phase was rendered acidic with conc. hydrochloric acid and extracted with ethyl acetate. After drying the ethyl acetate phase over magnesium sulfate, the solvent was distilled off under reduced pressure and the residue was crystallized from ether to give 1.21 g of white crystals.

m.p. 154.5°–155° C., yield: 97.0%

EXAMPLE 7

2-{1-(4-Phenoxyphenyl)propan-1-ylidene}-5-methyl-1,3,5-dithiazine (Compound No. 22)

5-Methyl-1,3,5-dithiazine, 2.7 g, was dissolved in 20 ml of tetrahydrofuran and 14 ml of 1.6 mole hexane solution of n-butyl lithium was dropwise added to the solution in an argon flow at −73° C. The mixture was stirred at the same temperature for an hour. Then, 2.4 g of trimethylsilyl chloride was dropwise added to the mixture at the same temperature. After completion of the dropwise addition, the temperature of the reaction mixture was gradually elevated to 0° C. and then stirred for 90 minutes to give crude 2-trimethylsilyl-5-methyl-1,3,5-dithiazine. Without purifying the crude product, 14 ml of 1.6 mole hexane solution of n-butyl lithium was dropwise added thereto at −10° C. followed by stirring for 30 minutes. After cooling to −73° C., a solution of 4.5 g of 4-phenoxypropiophenone in 10 ml of tetrahydrofuran was dropwise added. After completion of the dropwise addition, the temperature was gradually elevated to room temperature followed by stirring for 14 hours. After saturated sodium chloride aqueous solution was added to the mixture, it was extracted with chloroform. After drying the chloroform phase over magnesium sulfate, the solvent was distilled off under reduced pressure and the residue was purified by silica gel column chromatography (chloroform : hexane =2 : 1) to give 5.5 g of the product.

m.p. 96.0°–96.5° C., yield: 80.5%

EXAMPLE 8

1,1-Bis(methylthio)-2-(4-phenoxyphenyl)-1 butene (Compound No. 96)

Trimethylsilyl-bis(methylthio)methane, 2.65 g, was dissolved in 15 ml of tetrahydrofuran and 7 ml of 1.6 mole hexane solution of n-butyl lithium was dropwise added to the solution in an argon flow under ice cooling. The mixture was stirred at the same temperature for 30 minutes. After cooling to −73° C., a solution of 2.26 g of 4-phenoxypropiophenone in 5 ml of tetrahydrofuran was dropwise added to the mixture. Then, the temperature was gradually elevated to room temperature followed by stirring for 16 hours. After saturated sodium chloride aqueous solution was added to the mixture, it was extracted with chloroform. After drying the chloroform phase over magnesium sulfate, the solvent was distilled off under reduced pressure and the residue was purified by silica gel column chromatography (chloroform : hexane =1 : 1) to give 3.04 g of the oily product.

$n_D^{19.5}$ 1.5988, yield: 96.2%

EXAMPLE 9

2-[1-{4-(4-Methoxyphenoxy)phenyl}ethan-1-ylidene]-1,3-dithiane-1-oxide (Compound No. 26)

2-[1-{4-(4-Methoxyphenoxy)phenyl}ethan-1-ylidene]-1,3-dithiane, 5 g, was dissolved in a solvent mixture of 100 ml of tetrahydrofuran and 50 ml of methanol and, 15 g of an aqueous solution containing 2.45 g of oxon was dropwise added to the solution under ice cooling. After stirring for an hour at the same temperature, water was added to the reaction mixture followed by extraction with chloroform. The organic phase was washed with a sodium thiosulfate aqueous solution and then with water. After drying over magnesium sulfate, the solvent was distilled off under reduced pressure and the residue was purified by silica gel column chromatography (methylene chloride) to give 0.85 g of white crystals.

m.p. 136°–138.0° C.; yield: 16.2%

EXAMPLE 10

2-[1-{4-(4-n-Hexyloxyphenoxy)phenyl}ethan-1-ylidene1,3-dithiane (Compound No. 30)

2-Diethylphosphoryl-1,3-dithiane, 2.82 g, was dissolved in 30 ml of tetrahydrofuran and 7.0 ml of 1.6 mole hexane solution of n-butyl lithium was dropwise added to the solution in an argon flow at −73° C. The mixture was stirred for 1 hour and a solution of 2.9 g of 4-(4-n-hexyloxyphenoxy)acetophenone in 10 ml of tetrahydrofuran was dropwise added to the mixture at the same temperature. The reaction mixture was gradually warmed to room temperature overnight. Then the reaction mixture was poured onto ice water and the resulting mixture was extracted with chloroform. After drying the chloroform phase over magnesium sulfate, the solvent was distilled off under reduced pressure and the residue was purified by silica gel column chromatography (acetone : hexane =1 : 3) to give 3.41 g of the oily product.

$N^{11.5}$ 1.6091, Yield: 88.7%

EXAMPLE 11

2-[1-{4-(3-N-Methylpiperazinopropyloxy)phenoxy]-phenyl}ethan-1-ylidene]-1,3-dithiane (Compound No. 43)

2-Diethylphosphoryl-1,3-dithiane, 3.16 g, was dissolved in 30 ml of tetrahydrofuran and 7.0 ml of 1.6 mole hexane solution of n-butyl lithium was dropwise added to the solution in an argon flow at −73° C. The mixture was stirred for 1 hour and a solution of 2.72 g of 4-[4-(3-N-methylpiperazino-propyloxy)phenoxy]acetophenone in 10 ml of tetrahydrofuran was dropwise added to the mixture at the same temperature. Then the reaction mixture was gradually warmed to room temperature overnight. Then the reaction mixture was poured onto ice water and the resulting mixture was extracted with chloroform. After drying the chloroform phase over magnesium sulfate, the solvent was distilled off under reduced pressure and the residue was purified by silica gel column chromatography (chloroform : methanol =2 : 3) to give 2.50 g of the oily product.

$n^{28.5}$ 1.6069, Yield: 86.0%

EXAMPLE 12

2-[1-{4-(3-N-Methylpiperazinopropyloxy)phenoxy}phenyl]ethan-1-ylidene]-1,3-dithiane citric acid salt (Compound No. 44)

2-[1-{4-(3-N-Methylpiperazinopropyloxy)phenoxy}phenyl]ethan-1-ylidene]-1,3-dithiane, 0.50 g, was dissolved in 20 ml of ether and a solution of 0.21 g of citric acid in 20 ml of ether was dropwise added under water cooling. The precipitated crystals were collected by filtration, washed with ether to give 0.54 g of the desired product.

m.p. 187.0°-188.0° C., Yield: 77.0%

EXAMPLE 13

Ethyl 4-[4-{1-(1,3-Dithian-2-ylidene)ethan-1-yl}phenoxy]benzoate (Compound No. 74)

2-Diethylphosphoryl-1,3-dithiane, 1.90 g, was dissolved in 20 ml of tetrahydrofuran and 4.5 ml of 1.6 mole hexane solution of n-butyl lithium was dropwise added to the solution in an argon flow at −73° C. The mixture was stirred for 1 hour and a solution of 2.9 g of ethyl 4-(4-acetylphenoxy)beonzoate in 10 ml of tetrahydrofuran was dropwise added to the mixture at the same temperature. The reaction mixture was gradually warmed to room temperature overnight. Then the reaction mixture was poured onto ice water and the resulting mixture was extracted with chloroform. After drying the chloroform phase over magnesium sulfate, the solvent was distilled off under reduced pressure and the residue was purified by silica gel column chromatography (acetone : hexane =1 : 4) to give 1.95 g of white crystals.

m.p. 57.0°-58.0° C., Yield: 88.7%

EXAMPLE 14

2-[1-(4-Benzylphenyl)propan-1-ylidene]-1,3-dithiane (Compound No. 24)

2-Diethylphosphoryl-1,3-dithiane, 2.82 g, was dissolved in 30 ml of tetrahydrofuran and 7.0 ml of 1.6 mole hexane solution of n-butyl lithium was dropwise added to the solution in an argon flow at −73° C. The mixture was stirred for 1 hour. Then, a solution of 2.9 g of 4-benzylacetonphenone in 10 ml of tetrahydrofuran was dropwise added to the mixture at the same temperature. The reaction mixture was gradually warmed to room temperature overnight. Then the reaction mixture was poured onto ice water and the resulting mixture was extracted with chloroform. After drying the chloroform phase over magnesium sulfate, the solvent was distilled off under reduced pressure and the residue was purified by silica gel column chromatography (chloroform : hexane=1:3) to give 2.22 g of white crystals.

m.p. 46.5°-48.0° C., Yield: 68.0%

EXAMPLE 15

2-[1-{4-(4-n-Fluorophenoxy)phenyl}ethan-1-ylidene]-1,3-dithiane (Compound No. 2)

2-Diethylphosphoryl-1,3-dithiane, 1.2 g, was dissolved in 15 ml of tetrahydrofuran and 3.0 ml of 1.6 mole hexane solution of n-butyl lithium was dropwise added to the solution in an argon flow at −73° C. The mixture was stirred for 1 hour and a solution of 0.9 g of 4-(4-fluorophenoxy)acetophenone in 5 ml of tetrahydrofuran was dropwise added to the mixture at the same temperature. The reaction mixture was gradually warmed to room temperature overnight. Then the reaction mixture was poured onto ice water and the resulting mixture was extracted with chloroform. After drying the chloroform phase over magnesium sulfate, the solvent was distilled off under reduced pressure and the residue was purified by silica gel column chromatography (chloroform : hexane =1 : 1) to give 1.20 g of the pasty product.

Yield: 92.1%

EXAMPLE ;16

1-Dimethylamino-2-[1-[4-(4-n-fluorophenoxy)-phenyl}ethan-1-ylidene]-1,3-dithiane (Compound No. 89)

2-Trimethylsillyl-1,3-dithiane, 1.20 g, was dissolved in 10 ml of tetrahydrofuran and 3.0 ml of 1.6 mole hexane solution of n-butyl lithium was dropwise added to the solution in an argon flow at −10° C. Then the mixture was cooled at -73° C. and a solution of 0.93 g of 4-(4-methoxyphenoxy)acetophenone in 10 ml of tetrahydrofuran was dropwise added to the mixture at the same temperature. The reaction mixture was gradually warmed to room temperature overnight. Then the reaction mixture was poured onto ice water and the resulting mixture was extracted with chloroform. After drying the chloroform phase over magnesium sulfate, the solvent was distilled off under reduced pressure and the residue was purified by silica gel column chromatography (ethyl acetate : hexane =3 : 2) to give 0.60 g of white crystals.

m.p 92.0°-93.0° C., Yield: 47.7%

EXAMPLE 17

2-[1-{4-(4-Methylsulfinylphenoxy)phenyl}ethan-1-ylidene]-1,3-dithiane (Compound No. 80)

2-Diethylphosphoryl-1,3-dithiane, 2.05 g, was dissolved in 25 ml of tetrahydrofuran and 5.0 ml of 1.6 mole hexane solution of n-butyl lithium was dropwise added to the solution in an argon flow at −73° C. The mixture was stirred for 1 hour. Then, a solution of 1.79 g of 4-(4-methylsulfinylphenoxy)-acetophenone in 10 ml of tetrahydrofuran was dropwise added to the mixture at the same temperature. The reaction mixture was gradually warmed to room temperature overnight. Then the reaction mixture was poured onto ice water and the resulting mixture was extracted with chloroform. After drying the chloroform phase over magnesium sulfate, the solvent was distilled off under reduced pressure and the residue was purified by silica gel column chromatography (chloroform : hexane =2 : 1) to give 2.07 g of white crystals.

m.p. 131.5°-132.5° C., Yield: 83.0%

EXAMPLE 18

2-[1-{4-(4-Hydroxyphenylthio)phenyl}ethan-1-ylidene]-1,3-dithiane (Compound No. 82)

2-Diethylphosphoryl-1,3-dithiane, 3.80 g, was dissolved in 30 ml of tetrahydrofuran and 9.2 ml of 1.6 mole hexane solution of n-butyl lithium was dropwise added to the solution in an argon flow at −73° C. The mixture was stirred for 1 hour and a solution of 0.90 g of 4-(4-hydroxyphenylthio)acetophenone in 10 ml of tetrahydrofuran was dropwise added to the mixture at the same temperature. The reaction mixture was gradually warmed to room temperature overnight. Then the reaction mixture was poured onto ice water and the resulting mixture was extracted with chloroform. After drying the chloroform phase over magnesium sulfate, the solvent was distilled off under reduced pressure and the residue was purified by silica gel column chromatography (ethyl acetate : hexane =2 : 1) to give 0.94 g of the oily product.

m.p. 113.0°-114.0° C., Yield: 74.0%

EXAMPLE 19

2-[1-{4-(3,4-Dimethoxyphenoxy)phenyl}ethan-1-ylidene]-1,3-dithiane (Compound No. 7)

2-Diethylphosphoryl-1,3-dithiane, 2.05 g, was dissolved in 20 ml of tetrahydrofuran and 5.0 ml of 1.6 mole hexane solution of n-butyl lithium was dropwise added to the solution in an argon flow at −73° C. The mixture was stirred for 1 hour and a solution of 1.91 g of 4-(3,4-dimethoxyphenoxy)acetophenone in 10 ml of tetrahydrofuran was dropwise added to the mixture at the same temperature. The reaction mixture was gradually warmed to room temperature overnight. Then the reaction mixture was poured onto ice water and the resulting mixture was extracted with chloroform. After drying the chloroform phase over magnesium sulfate, the solvent was distilled off under reduced pressure and the residue was purified by silica gel column chromatography (chloroform : hexane = 1 : 1) to give 1.81 g of the white crystals.

m.p. 73.5°-75.5° C., Yield: 69.0%

In the following Examples, all parts are by weight. The kinds and proportions of ingredients can be widely varied.

EXAMPLE 20

A powder or fine granular preparation was prepared by mixing uniformly and pulverizing or granulating finely the following ingredients:

| Compound 2 | 10 parts |
| Ground magnesium oxide | 10 parts |
| Lactose | 80 parts |

EXAMPLE 21

A powder was prepared according to Example 20 by using the following ingredient:

| Compound 6 | 10 parts |
| Synthetic aluminum silicate | 10 parts |
| Calcium hydrogenphosphate | 5 parts |
| Lactose | 75 parts |

EXAMPLE 22

Granules were prepared by kneading together uniformly, grinding, granulating the following ingredients, drying the resultant, and then sieving:

| Compound 11 | 50 parts |
| Starch | 10 parts |
| Lactose | 15 parts |
| Crystalline cellulose | 20 parts |
| Polyvinyl alcohol | 5 parts |
| Water | 30 parts |

EXAMPLE 23

Tablets having a diameter of 10 mm were prepared by mixing 99 parts of the granules obtained in Example 22 with 1 part of calcium stearate, and compression-molding the resulting mixture.

EXAMPLE 24

Granules were prepared in the same manner as in Example 22 except for using the following ingredients:

| Compound 20 | 78 parts |
| Polyvinyl alcohol | 2 parts |
| Lactose | 20 parts |
| Water | 30 parts |

To 90 parts of the granules obtained was added 10 parts of crystalline cellulose, and the resulting mixture was compression-molded into tablets having a diameter of 8 mm. Then, the tablets were made into dragees by use of suitable amounts of a mixed suspension of syrup, gelatin and precipitated calcium carbonate and coloring matter.

EXAMPLE 25

An injection was prepared by mixing by heating, and then sterilizing the following ingredients:

| Compound 98 | 0.5 parts |
|---|---|
| Nonionic surface active agent | 2.5 parts |
| Physiological saline | 97 parts |

EXAMPLE 26

Capsules were prepared by packing the powder obtained in Example 21 into commercially available capsular containers.

Next, test examples of this invention are shown below.

Test Example

Serum lipid reducing effect (in rat)

Test method: A high-cholesterol diet (HCD) was given the 4-week-old male Wistar strain rats for 7 days. On the fourth day after the beginning of this feeding, blood was drawn from the plexus venosus in eyeground by means of a capillary tube (heparin-treated, 75 mm, Drummond Scientific) without fasting, and plasma was separated from the blood. The plasma total cholesterol concentration (p-TC) before the beginning of administration of a compound to be treated was measure, and the animals were divided into groups so as to minimize the scatter of p-TC values in each group. Each compound to be treated and a reference compound were individually suspended in a 2% (W/V) aqueous gum arabic solution in a concentrating of 0.6 or 6.0% (W/V), and each of the suspension thus prepared was administered every day in an amount of 5 ml/kg/day for the latter 4 days of the above 7 days. Commercial normal diet was orally administered to a control group for 7 days, a 2% aqueous gum arabic solution was similarly administered thereto for the latter 4 days of these 7 days. After fasting for 16 hours from 8 hours after the last administration of the compound to be tested, blood was drawn from the carotid artery under ether anaesthesia and serum was separated from the blood and analyzed for lipid. The plasma and serum total cholesterol concentration (p-TC and s-TC) was measured by a an automatic analyzer enzymatically, and the cholesterol reducing effect of the compound to be tested was calculated by the following equation and evaluated as TC reduction percentage:

$$TC \text{ reduction percentage (\%)} = \frac{TC_b - TC_c}{TC_b - TC_a} \times 100$$

wherein
- $TC_a$ = the total cholesterol concentration of the control group.
- $TC_b$ = the total cholesterol concentration of the group to which a high-cholesterol diet was given.
- $TC_c$ = the total cholesterol concentration of the group to which each compound of this invention is administered.

The results obtained are shown in Table 2.

TABLE 2

| Compound No. | Cholesterol reduction percentage (%) |
|---|---|
| 1 | 18 |
| 2 | 70 |
| 4 | 34 |
| 5 | 52 |
| 6 | 75 |
| 10 | 59 |
| 11 | 65 |
| 13 | 23 |
| 14 | 36 |
| 20 | 55 |
| 24 | 38 |
| 25 | 48 |
| 26 | 17 |
| 28 | 64 |
| 29 | 78 |
| 30 | 78 |
| 31 | 60 |
| 32 | 40 |
| 33 | 55 |
| 34 | 34 |
| 35 | 28 |
| 36 | 68 |
| 37 | 84 |
| 38 | 73 |
| 40 | 64 |
| 41 | 27 |
| 42 | 64 |
| 43 | 29 |
| 44 | 5 |
| 46 | 30 |
| 50 | 51 |
| 51 | 58 |
| 52 | 20 |
| 54 | 29 |
| 55 | 53 |
| 56 | 6 |
| 57 | 91 |
| 58 | 15 |
| 59 | 80 |
| 61 | 15 |
| 63 | 29 |
| 64 | 54 |
| 66 | 13 |
| 67 | *31 |
| 69 | 31 |
| 70 | 11 |
| 74 | 50 |
| 75 | 9 |
| 76 | 32 |
| 77 | 81 |
| 78 | 84 |
| 80 | 32 |
| 81 | 47 |
| 87 | 29 |
| 88 | 47 |
| 90 | 26 |
| 94 | 8 |
| 98 | 51 |
| 101 | 37 |
| 102 | 40 |
| Reference compound A | −60 |
| Reference | 1 |

TABLE 2-continued

| Compound No. | Cholesterol reduction percentage (%) |
|---|---|
| compound B | |

*The dose of 100 mg.
Note:
Reference compound A:
(commercially available)

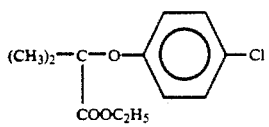

Reference compound B:

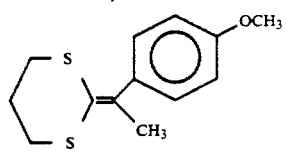

As shown in Table 2, the compounds of this invention show a cholesterol-reducing effect and have a hypolipomedia activity.

Some of them compounds of this invention such as compound No. 63, 67 and 84 showed strong anti-oxidant activity. Since oxidative modefication of serum lipids is known to be one of causes of arterioseroosis, the compounds of this invention can be used to prevent arteriosclerosis.

While the invention has been described in detail and with reference to specific embodiments thereof, it is apparent to one skilled in the art that various changes and modifications can be made therein without departing from the spirit and the scope of the present invention.

What is claimed is:

1. A ketenedithioacetal derivative represented by general formula (I):

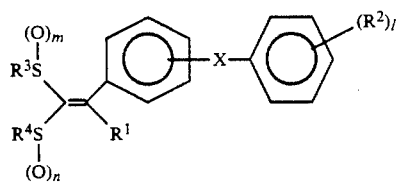

wherein $R^1$ represents a $C_1$- to $C_4$-alkyl group, a $C_2$- to $C_7$-alkoxycarbonyl $C_1$- to $C_6$-alkyl group, a di($C_1$- to $C_4$-alkyl)amino-$C_1$- to $C_6$-alkyl group or a carboxy-$C_1$- to $C_6$-alkyl group; $R^2$, which may be the same or different, independently represents a hydrogen atom, a halogen atom, a $C_1$- to $C_6$-alkyl group (whose group is optionally substituted with a $C_2$- to $C_7$-alkoxycarbonyl group, a $C_1$- to $C_4$-alkylsulfinyl group or a carboxy group), a hydroxy group, a $C_1$- to $C_{16}$-alkoxy group (whose alkyl moiety is optionally substituted with a $C_1$- to $C_4$-alkoxycarbonyl group, a carboxy group, a di-$C_1$- to $C_4$-alkylamino group, a N-$C_1$- to $C_4$-alkyl-substituted piperazino group, a hydroxy group or a nitroxy group), a $C_2$- to $C_7$-alkylcarbonyloxy group, a methylenedioxy group, a $C_2$- to $C_7$-alkoxycarbonyl group, a carboxy group, a cyano group, a $C_1$- to $C_4$-alkylthio group or a $C_1$- to $C_4$-alkylsulfinyl group; $R^3$ and $R^4$ are combined together to form a $C_2$- to $C_4$-alkylene group; X represents an oxygen atom, a sulfur atom or a methylene group; l represents an integer of 1 to 3; and m and n represent 0 or an integer of 1, or its pharmaceutically acceptable salts.

2. A ketenedithioacetal derivative according to claim 1, wherein $R^1$ represents a lower alkyl group, a lower alkoxycarbonylalkyl group or a carboxyalkyl group; $R^2$, which may be the same or different, independently represents a hydrogen atom, a halogen atom, a lower alkyl group, a hydroxy group or a lower alkoxy group; $R^3$ and $R^4$ may be combined together to form a $C_2$ to $C_4$ alkylene group; X represents an oxygen atom or a methylene group; l is an integer of 1 to 3; and m and n are 0 or an integer of 1.

3. A ketenedithioacetal derivative according to claim 1, wherein $R^1$ represents a $C_1$- to $C_6$-alkyl group, a $C_2$- to $C_7$-alkoxycarbonyl $C_1$- to $C_6$alkyl group, or a di($C_1$- to $C_4$-alkyl)amino-$C_1$- to $C_6$-alkyl group or a carboxy-$C_1$- to $C_6$-alkyl group; $R^2$, which may be the same or different, independently represents a hydrogen atom, a halogen atom, a $C_1$- to $C_6$-alkyl group (whose group is optionally substituted with a $C_2$- to $C_7$-alkoxycarbonyl group, a $C_1$- to $C_4$-alkylsulfinyl group or a carboxyl group), a hydroxy group, a $C_1$- to $C_{16}$-alkoxy group (whose alkyl moiety is optionally substituted with a $C_2$- to $C_7$-alkoxycarbonyl group or a carboxyl group, a di-$C_1$- to $C_4$-alkylamino group, a N-$C_1$- to $C_4$alkyl-substituted piperazino group, a hydroxy group or a nitroxy group), a $C_2$- to $C_7$-alkylcarbonyloxy group, a methylenedioxy group, a $C_2$- to $C_7$-alkoxycarbonyl group, a carboxyl group, a cyano group, a $C_1$- to $C_4$-alkylthio group or a $C_1$- to $C_4$-alkylsulfinyl group; $R^3$ and $R^4$ are combined together to form a $C_2$- to $C_4$-alkylene group; S represents an oxygen atom, a sulfur atom or a methylene group; l represents an integer of 1 to 3; and m and n represent 0 or an integer of 1.

4. A ketenedithioacetal derivative according to claim 1, 2 or 3, which is 2-[1-{4-(4-methoxyphenoxyphenyl)}ethan-1-ylidene]1,3-dithiane, 2-[1-{4-(4-n-propoxyphenoxyphenyl)}ethan-1-ylidene]-1,3-dithiane, 2-[1-{4-(4i-propoxyphenoxyphenyl)}ethan-1-ylidene]-1,3-dithiane, 2-[1-{4-(4-(3-dimethylaminopropoxy)-phenoxyphenyl)}ethan-1-ylidene]-1,3-dithiane, 2-[1-{4-(4-phenoxyphenyl)}propan-1-ylidene]-1,3-dithiane, 2-[1-{4-(4-acetoxyphenoxyphenyl)}propan-1-ylidene]-1,3-dithiane, 2-[1-{4-(4-n-propoxyphenoxyphenyl)}propan-1-ylidene]-1,3-dithiane, 2-[1-{4-(3-methyl-4-hydroxyphenoxy)phenyl}ethan-1-ylidene]-1,3-dithiane, 2-[1-{4-(3,5-dimethyl-4-hydroxyphenoxy)phenyl}ethan-1-ylidene]-1,3-dithiane, 4-[4-{1-(1,3-dithian-2-ylidene)ethan-1-yl}phenoxy]phenoxyacetic acid, 4-[4-{1-(1,3-dithian-2-ylidene)ethan-1-yl}phenoxy]phenylacetic acid, 2-[1-{4-(4-hydroxyphenoxy)phenyl}ethan-1-ylidene]-1,3-dithiane, 2-[1-{4-(3-hydroxyphenoxy)phenyl}ethan-1-ylidene]-1,3-dithiane, 2-[1-{4-(3-methoxyphenoxy)phenyl}ethan-1-ylidene]-1,3-dithiane, ethyl 4-[4-{1-(1,3-dithian-2-ylidene)ethan-1-yl}phenoxy]benzoate, ethyl 4-[4-{1-(1,3-dithian-2-ylidene)ethan-1-yl}phenoxy]phenylacetate, 2-[1-{4-(3-methyl-4-hydroxyphenoxy)phenyl}ethan-1-ylidene]-1,3-dithiane, 2-[1-{4-(3,5-dimethyl-4-hydroxyphenoxy)phenyl}ethan-1-ylidene]-1,3-dithiane, 4-[4-{1-(1,3-dithian-2-ylidene)ethan-1-yl}phenoxy]phenoxybutyric acid and 2-[1-}4-(4-fluorophenoxy)phenyl}ethan-1-ylidene]-1,3-dithiane.

5. A pharmaceutical composition comprising a pharmaceutically acceptable diluent and as an active ingredient a ketenedithioacetal derivative represented by general formula (I):

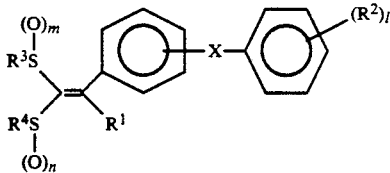

wherein $R^1$ represents a $C_1$- to $C_4$-alkyl group, a $C_2$- to $C_7$-alkoxycarbonyl $C_1$- to $C_4$-alkyl group, a di($C_1$- to $C_4$-alkyl)amino-$C_1$- to $C_6$-alkylamino group or a carboxy-$C_1$- to $C_4$-alkyl group; $R^2$, which may be the same or different, independently represents a hydrogen atom, a halogen atom, a $C_1$- to $C_6$-alkyl group (whose group is optionally substituted with a $C_2$- to $C_7$-alkoxycarbonyl group, a $C_1$- to $C_4$-alkylsulfinyl group or a carboxyl group), a hydroxy group, a $C_1$- to $C_{16}$-alkoxy group (whose alkyl moiety is optionally substituted with a $C_2$- to $C_7$-alkoxycarbonyl group, a carboxy group, a di-$C_1$- to $C_4$-alkylamino group, an N-$C_1$- to $C_4$-alkyl-substituted piperazino group, a hydroxy group or a nitroxy group), a $C_2$- to $C_7$-alkylcarbonyloxy group, a methylenedioxy group, a $C_2$- to $C_7$-alkoxycarbonyl group, a carboxyl group, a cyano group, a $C_1$- to $C_4$-alkylthio group or a $C_1$- to $C_4$-alkylsulfinyl group; $R^3$ and $R^4$ are combined together to form a $C_2$- to $C_4$-alkylene group; X represents an oxygen atom, a sulfur atom or a methylene group; l represents an integer of 1 to 3; and m and n represent 0 or an integer of 1, or its pharmaceutically acceptable salts.

6. A pharmaceutical composition according to claim 5, wherein $R^1$ represents a lower alkyl group, a lower alkoxycarbonylalkyl group or a carboxyalkyl group; $R^2$, which may be the same or different, independently represents a hydrogen atom, a halogen atom, a lower alkyl group, a hydroxy group or a lower alkoxy group; $R^3$ and $R^4$ may be combined together to form a $C_2$ to $C_4$ alkylene group; X represents an oxygen atom or a methylene group; l is an integer of 1 to 3; and m and n are 0 or an integer of 1.

7. A pharmaceutical composition according to claim 5, wherein $R^1$ represents a $C_1$- to $C_6$-alkyl group, a $C_2$- to $C_7$-alkoxycarbonyl $C_1$- to $C_6$-alkyl group, a di($C_1$- to $C_4$alkyl)amino-$C_1$- to $C_6$-alkylamino group or a carboxy-$C_1$- to $C_6$-alkyl group; $R_2$, which may be the same or different, independently represents a hydrogen atom, a halogen atom, a $C_1$- to $C_6$alkyl group (whose group is optionally substituted with a $C_2$- to $C_7$-alkoxycarbonyl group, a $C_1$- to $C_4$alkylsulfinyl group or a carboxyl group), a hydroxy group, a $C_1$- to $C_{16}$-alkoxy group (whose alkyl moiety is optionally substituted with a $C_2$- to $C_7$-alkoxycarbonyl group, a carboxyl group, a di-$C_1$- to $C_4$-alkylamino group, an N-$C_1$- to $C_4$-alkyl substituted piperazino group, a hydroxy group or nitroxy group), a $C_2$- to $C_7$-alkylcarbonyloxy group, a methylenedioxy group, a $C_2$- to $C_7$-alkoxycarbonyl group, a carboxyl group, a cyano group, a $C_1$- to $C_4$-alkylthio group or a $C_1$- to $C_4$-alkylsulfinyl group; $R^3$ and $R^4$ are combined together to form a $C_2$- to $C_4$-alkylene group; X represents an oxygen atom, a sulfur atom or a methylene group; l represents an integer of 1 to 3; and m and n represent 0 or an integer of 1.

8. A pharmaceutical composition according to claim 5, 6 or 7, wherein said ketenedithioacetal derivative is selected from 2-[1-{4-(4-methoxyphenoxyphenyl)}ethan-1-ylidene]-1,3-dithiane, 2-[1-{4-(4-n-propoxyphenoxyphenyl)}ethan-1-ylidene]-1,3-dithiane, 2-[1-{4-(4-i-propoxyphenoxyphenyl)}ethan-1-ylidene]-1,3-dithiane, 2-[1-{4-)4-(3-dimethylaminopropoxy)phenoxyphenyl)}ethan-1-ylidene]-1,3-dithiane, 2-[1-{4-(4-phenoxyphenyl)}propan-1-ylidene]-1,3dithiane, 2-[1-{4-(4-acetoxyphenoxyphenyl)}propan-1-ylidene]-1,3-dithiane, 2-[1-{4-(4-n-propoxyphenoxyphenyl)}propan-1-ylidene]1,3-dithiane, 2-[1-{4-(3-methyl-4-hydroxyphenoxy)phenyl}ethan-1-ylidene]-1,3-dithiane, 2-[1-{4-(3,5-dimethyl-4-hydroxyphenoxy)phenyl}ethan-1-ylidene]1,3-dithiane, 4-[4-{1-(1,3-dithian-2-ylidene)ethan-1-yl}phenoxy]phenoxyacetic acid, 4-[4-{1-(1,3-dithian-2-ylidene)ethan-1-yl}phenoxy]phenylacetic acid, 2-[1-{4-(4-hydroxyphenoxy)phenyl}ethan-1-ylidene]-1,3-dithiane, 2-[1-{4-(3-hydroxyphenoxy)phenyl}ethan-1-ylidene]-1,3-dithiane, 2-[1-{4-(3-methoxyphenoxy)phenyl}ethan-1-ylidene]-1,3-dithiane, ethyl 4-[4-{1-(1,3-dithian-2-ylidene)ethan-1-yl}phenoxy]benzoate, ethyl 4-[4-{1-(1,3-dithian-2-ylidene)ethan-1-yl}phenoxy]phenylacetate, 2-[1-{4-(3-methyl-4-hydroxyphenoxy)phenyl}ethan-1-ylidene]-1,3-dithiane, 2-[1-{4-(3,5-dimethyl-4-hydroxyphenoxy)phenyl}ethan-1-ylidene]-1,3-dithiane, 4-[4-{1-(1,3-dithiane-2-ylidene)ethan-1-yl}phenoxy]phenoxybutyric acid and 2-[1-{4-(4-fluorophenoxy)phenyl}ethan-1-ylidene-1,3-dithiane.

* * * * *